(12) United States Patent
Primus

(10) Patent No.: US 12,171,898 B2
(45) Date of Patent: Dec. 24, 2024

(54) BIOACTIVE MEDICAL CERAMIC CEMENT

(71) Applicant: NuSmile, Ltd, a Texas limited partnership, Houston, TX (US)

(72) Inventor: Carolyn M Primus, Sarasota, FL (US)

(73) Assignee: NuSmile, Ltd., Houston, TX (US)

( * ) Notice: Subject to any disclaimer, the term of this patent is extended or adjusted under 35 U.S.C. 154(b) by 749 days.

(21) Appl. No.: 17/251,192

(22) PCT Filed: Feb. 19, 2020

(86) PCT No.: PCT/US2020/018919
§ 371 (c)(1),
(2) Date: Dec. 10, 2020

(87) PCT Pub. No.: WO2021/167608
PCT Pub. Date: Aug. 26, 2021

(65) Prior Publication Data
US 2022/0047772 A1    Feb. 17, 2022

(51) Int. Cl.
*A61L 24/02* (2006.01)
*A61K 6/876* (2020.01)
*A61L 24/00* (2006.01)

(52) U.S. Cl.
CPC ............ *A61L 24/02* (2013.01); *A61K 6/876* (2020.01); *A61L 24/0015* (2013.01)

(58) Field of Classification Search
CPC .......... A61K 6/08; C04B 22/16; C04B 28/34; C09K 8/467; E21B 33/16

(Continued)

(56) References Cited

U.S. PATENT DOCUMENTS

| 6,620,232 | B1 | 9/2003 | Kraft et al. |
| 7,025,824 | B2 | 4/2006 | Axén et al. |

(Continued)

FOREIGN PATENT DOCUMENTS

| WO | 2004028577 A1 | 4/2004 |
| WO | 2008100452 A2 | 8/2008 |
| WO | 2008118096 A1 | 10/2008 |

OTHER PUBLICATIONS

Tan et al., "Calcium silicate/calcium aluminate composite biocement for bone restorative application: synthesis, characterisation and in vitro biocompatibility." Advances in Applied Ceramics 2016 vol. 115 No. 7; 384-390. (Year: 2016).*

(Continued)

*Primary Examiner* — Walter E Webb
(74) *Attorney, Agent, or Firm* — Keeling Law, LLC; Kenneth A. Keeling; Mark S. Solomon

(57) ABSTRACT

Bioactive, ceramic medical cements and methods for its use in treatment of bones and teeth in mammals are disclosed. This cement is non-exothermic and non-toxic, based upon setting of hydraulic ceramic compounds containing calcia, alumina, and silica phases. The self-hardening cement sets in vivo and in high humidity environments, and can be used in vivo without being easily washed out of the site. It also has dimensional stability, is resistant to acids present in an infection site or supragingivally, and has biocompatibility advantages of low inflammation and the formation of calcification layers in direct apposition to body tissue. Options include the addition of various radiopaque materials, and a variety of delivery systems including powder and liquid, capsule or pouch delivery, multiple pastes, or a unitary paste.

20 Claims, 1 Drawing Sheet

(58) Field of Classification Search
USPC .......................................... 424/423; 523/116
See application file for complete search history.

(56) References Cited

U.S. PATENT DOCUMENTS

| | | | |
|---|---|---|---|
| 7,244,301 B2 | 7/2007 | Axén et al. | |
| 7,501,018 B2 | 3/2009 | Engqvist et al. | |
| 7,682,445 B2 | 3/2010 | Hermansson et al. | |
| 7,867,329 B2 | 1/2011 | Hermansson et al. | |
| 7,892,342 B2 | 2/2011 | Primus | |
| 8,475,811 B2 | 7/2013 | Yang et al. | |
| 8,545,620 B2 | 10/2013 | Frenkenberger et al. | |
| 8,778,377 B2 | 7/2014 | Hermansson et al. | |
| 9,668,825 B2 | 6/2017 | Chow et al. | |
| 9,676,665 B2 | 6/2017 | Engqvist et al. | |
| 10,154,945 B2 | 12/2018 | Jang et al. | |
| 2003/0220414 A1 | 11/2003 | Axén et al. | |
| 2004/0117030 A1 | 6/2004 | Axén et al. | |
| 2005/0263036 A1 | 12/2005 | Primus | |
| 2006/0024348 A1 | 2/2006 | Engqvist et al. | |
| 2008/0085948 A1* | 4/2008 | Primus | A61K 6/78 523/116 |
| 2008/0213337 A1 | 9/2008 | Hermansson et al. | |
| 2008/0299093 A1* | 12/2008 | Yang | A61K 6/853 106/661 |
| 2009/0192513 A1 | 7/2009 | Hermansson et al. | |
| 2010/0092924 A1 | 4/2010 | Mongiorgi et al. | |
| 2011/0308428 A1* | 12/2011 | Munoz Viveros | A61K 6/838 106/35 |
| 2017/0072095 A1 | 3/2017 | Engqvist et al. | |
| 2018/0171204 A1* | 6/2018 | Agapiou | C04B 28/34 |
| 2021/0298998 A1 | 9/2021 | Oh et al. | |
| 2022/0117855 A2 | 4/2022 | Oh et al. | |

OTHER PUBLICATIONS

Mour et al., "Advances in Porous Biomaterials for Dental and Orthopaedic Applications." Materials 2010, 3, 2947-2974. (Year: 2010).*

Parirokh et al., Mineral Trioxide Aggregate: A Comprehensive Literature Review—Part III: Clinical Applications, Drawbacks, and Mechanism of Action, Journal of Endodontics, Mar. 2010.

Primus et al., Bioactive Tri/dicalcium Silicate Cements for Treatment of Pulpal and Periapical Tissues, Acta Biomater, Sep. 15, 2020.

Saxena et al., Biocompatability of root-end filling materials: recent update, Restorative Dentistry & Endodontics, Aug. 23, 2013.

Tan et al., Calcium silicate/calcium aluminate composite biocement for bone restorative application: synthesis, characterization and in vitro biocompatibility, Advances in Applied Ceramics, Apr. 6, 2016.

European Search Opinion and Supplemental EU Search Report, EP4106711, Nov. 10, 2023.

* cited by examiner

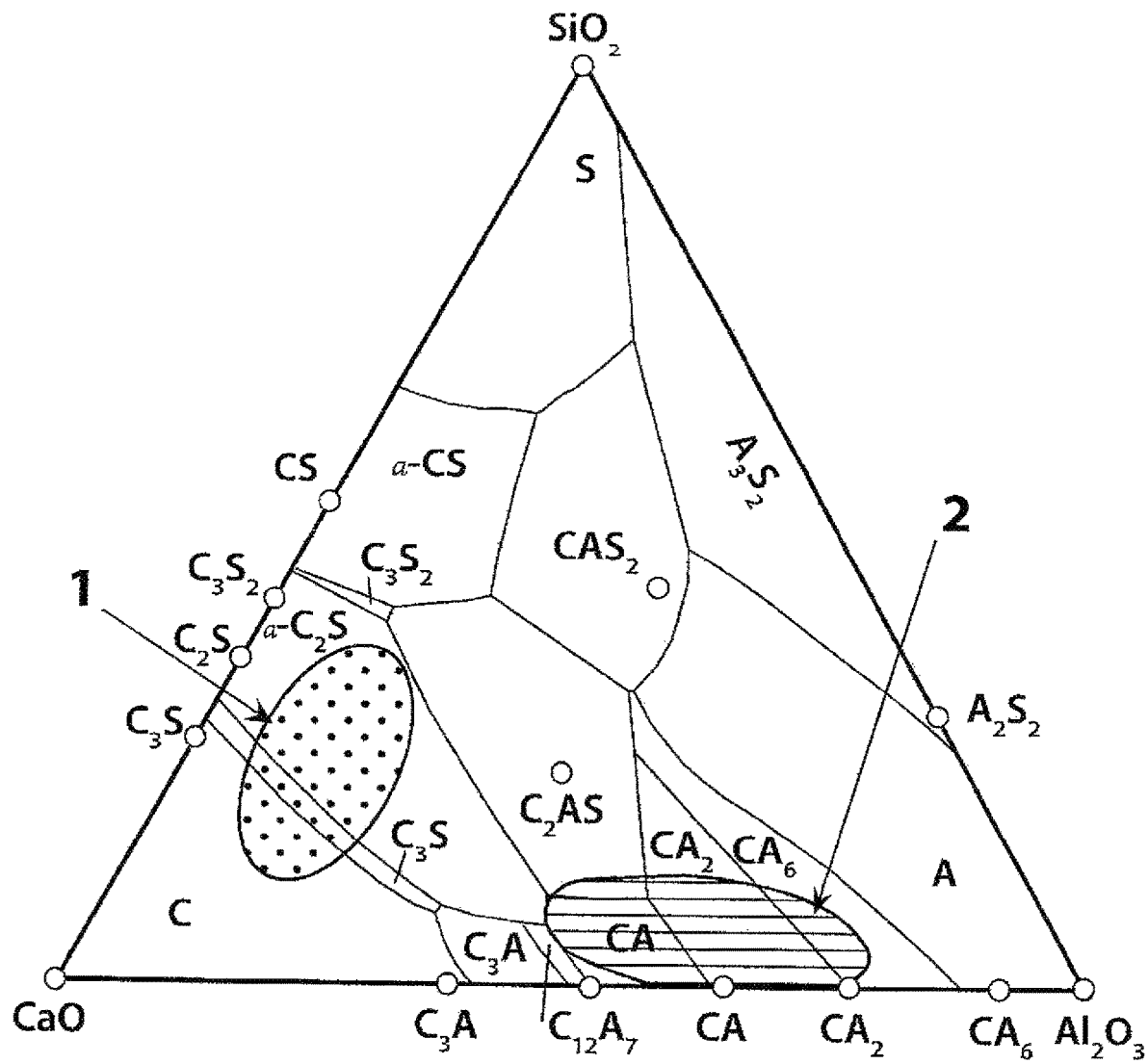

BIOACTIVE MEDICAL CERAMIC CEMENT

CROSS-REFERENCES TO RELATED APPLICATIONS

NONE

STATEMENT REGARDING FEDERALLY SPONSORED RESEARCH OR DEVELOPMENT

NONE

TECHNICAL FIELD

This invention is in the field of medical materials and methods therefor, such as those used in orthopedic, dental, or veterinary applications. Specifically, this invention is a new and versatile bioactive medical ceramic cement that is hydraulic and is also characterized by combinations of calcia, silica, and alumina-containing compounds. The present invention cements disclosed herein are biocompatible, dimensionally stable, have the advantage of setting at room temperature or body temperature without raising the local temperature during setting, as well as the further advantage of being more resistant to acids present in an infection site or supragingivally; this combination of features providing distinct and important advancements in the field, as will be noted in greater detail below, including advantages that are significant improvements over polymethylmethacrylate bone cements and other tricalcium silicate and dicalcium silicate medical device cements in common medical use today. Furthermore, the bioactive ceramic cements of the present invention disclosed herein have other biocompatibility advantages over polymethylmethacrylate, calcium hydroxide-containing preparations, epoxy or polyvinyl siloxane or zinc oxide-eugenol materials, including low inflammation, the formation of calcific layers in direct apposition to the body tissues (bioactivity), and osteogenesis. Optional additions to the bioactive medical ceramic cements of the present invention may include, but are not limited to radiopaque powders, including radiopaque glass.

The present invention is a powdered, bioactive ceramic material that may be placed directly in vivo, premixed as a ready-to-use paste using one or more non-aqueous organic or inorganic fluids or gels, or mixed by a medical professional prior to use for various medical applications, including but not limited to bone fixation, filling of bone defects, implant fixation such as joint replacements, or use in vertebroplasty or kyphoplasty procedures. In dentistry, the present invention is suitable for procedures involving vital pulp therapy or other endodontic procedures. Vital pulp procedures include pulp-capping, lining a cavity after caries excavation, base under another restorative material, pulpotomies, apexification, and regenerative endodontics. Other endodontic procedures include root-end filling, pulp-capping, iatrogenic perforation sealing, resorption, root canal sealing with or without gutta percha, endodontic post cementation, cementation of prosthetic devices, cementation of orthodontic devices, or dental ridge augmentation. For veterinary use, the same treatment issues exist for domesticated and specialty animals including those in protected reserves and zoos, and the present invention is also suitable for such application.

BACKGROUND ART

Bones and teeth suffer from attrition, injury, breakage, disease or infection, which require treatment. In many biomedical applications, a cement-like material is needed for the treatment and thereafter the material is preferably non-resorbable by the body, becoming a barrier or inhibitor to bacteria, restoring anatomical form or attaching another device. In other applications, such as bone grafting, a resorbable material may be needed. The present invention can be prepared/adapted for use in both applications.

In medicine, bone cements are used for the fixation of bone fragments or artificial joints, and the most commonly used cement is based on polymethylmethacrylate (PMMA) [Ref 1, Vaishya et. al], even though it is not bioactive, does not bond to bone, and may cause localized inflammation.

In dentistry, early childhood caries is a world-wide epidemic and is the most prevalent and chromic disease of childhood [Ref 2, Fung et. al]. When procedures such as a pulpotomy, or partial pulpotomy are performed in primary teeth, pediatric dentists have commonly placed formocresol on the remaining pulp. Although usually successful at maintaining the tooth, the formocresol has a fixative effect on the cells, toxicity and an undesirable permeating odor. A global increase also exists in dental caries prevalence in adults' permanent teeth, as well as root surfaces [Ref 3, Bagramian et. al] and caused by trauma, wear, or iatrogenically. Ideally, the pulp forms a dentinal bridge over the exposed pulp when treated. In both children and adults, more effective means are needed to treat chronic and progressive dental disease and restorative treatments. Ceramic cements denoted as mineral trioxide aggregate, MTA, have been used. MTA is a generic marketing name that denotes tricalcium silicate and dicalcium silicate cement particles with a radiopaque additive. This cement has the advantages of bioactivity, because it forms calcium hydroxide during setting. The calcium hydroxide is embedded in a hard cement and provides antimicrobial and bioactive properties. Clinical evidence has shown that the tri/dicalcium silicate cements are superior to any other pulpotomy treatment. The present invention is believed to go a step further and overcome the problems of slow setting and acid vulnerability that occur when tri/dicalcium silicate cements are applied.

In non-surgical root canal (endodontic) treatment, the pulp is extirpated and the root canals of the tooth are filled with an inert material that limits the ingress of any bacteria from the coronal region through the roots of the tooth into the alveolar bone. Commonly, gutta percha points and root canal walls are coated with a sealer material and placed in the prepared root canals, a process called obturation. Less commonly, the entire root canal is obturated with a material. Ideally the body should heal and seal the orifices at apex of the roots that formerly conducted the blood vessels and nerves into the pulp. If the aforementioned therapy is not successful, the tooth may be retreated in the same manner or treated surgically, through retrograde procedures, to maintain the non-vital tooth in the patient for their immediate comfort, minimal cost and overall dental health.

On occasion, an iatrogenically perforated root canal may be caused by the dentist during non-surgical endodontic treatment that creates a communication between the pulpal chamber and the alveolar bone surrounding the root. Such a passage must be sealed. The state-of-the art procedure is to fill it with tri/dicalcium silicate cements. However, infected sites may require more than one treatment with the tri/dicalcium silicate cements. The same issue of communication from the inside to the outside of the root may arise with root resorption, internal, external or cervical. Cervical root resorption has been commonly treated with Geristore® resin ionomer cement. Calcium silicate cements have not been used for this supragingival indication where contact with the oral cavity may occur; otherwise acids in the oral cavity may gradually dissolve the cement.

Dental materials based on tricalcium silicate and dicalcium silicate have been very effectively used for these above-described medical conditions. The most popular and reliable material for this surgical endodontic use has been based on Mineral Trioxide Aggregate (MTA), (U.S. Pat. No. 5,415,547 B1, (1995, Torabinejad & White), U.S. Pat. No. 5,769,638 B1 (1998, Torabinejad & White) and U.S. Pat. No. 7,892,342 B2 (2011, Primus), which have been commercialized as ProRoot® MTA and tooth-colored ProRoot® MTA by Dentsply Sirona. These products are primarily based on tricalcium silicate and dicalcium silicate and bismuth oxide, with lesser amounts of tricalcium aluminate and tetracalcium aluminoferrite. MTA's utility and properties have been reviewed in the Journal of Endodontics in 2010 [Ref 4, Parirokh et. al]. A recent review describes this type of material from a scientific point of view: Bioactive tri/dicalcium silicate cements for treatment of pulpal and periapical tissues [Ref 5, Primus]. Both reviews identify the shortcomings of MTA use.

Although prior art believed relevant to the present invention includes the patented inventions described below, none has all the advantages or the same composition of the present invention. Jang et. al. (U.S. Pat. No. 10,154,945 B2, 2018) disclosed a single paste hydraulic dental filling composition that contains a hygroscopic clay, is finer than 3 μm of average particle size, and comprises calcium oxide or calcium hydroxide as a component. The present invention does not need a hygroscopic clay, may have a coarser particle size than 3 μm, and doesn't comprise CaO or $Ca(OH)_2$. Chow and Takagi (U.S. Pat. No. 9,101,436 B2, 2015) disclosed an endodontic material with organic hydrogel formers, which are not necessary in the present invention, and Chow did not include the calcium aluminate cement combined with calcium silicate cement. Also, the seven-day shelf life without hardening (see Chow Claim 4) is too short to be useful, whereas the present invention has an extended shelf life of about 3 years. Chow and Takagi also disclosed in U.S. Pat. No. 9,259,439 B2 (2016) a dual-phase bone cement based on calcium phosphate, which is not a component herein. Berger (US 2019/0298621 A1, 2019) disclosed a method for reducing inflammation and treating vital pulp or periodontal tissue and a premixed "dicalcium silicate, tricalcium silicate and a mixture thereof" with water-soluble polymers and oil. A dental material patented by Primus et. al (U.S. Pat. No. 8,658,712, 2014) included hydroxyapatite powder with hydraulic powders, without mentioning monocalcium aluminate cement. Primus, Gutmann, Breuer and Jefferies (U.S. Pat. No. 9,801,792 B2, 2017) disclosed a method that included mixing a composition of hydraulic powder and a water-based liquid that required a water-soluble polymer and a surfactant, unlike the present invention. U.S. Pat. No. 9,925,125 B2 (Primus et. al., 2018) also disclosed a hydraulic powder and water-based liquid combination.

Yang in U.S. Pat. No. 8,475,811 (2003) disclosed a premixed hydraulic paste containing "at least one calcium silicate compound, in an amount in the range from about 20% to about 95%", whereas in this invention, the amount of calcium silicate compounds in pastes is less than 20%. Jang et. al. in U.S. Pat. No. 10,154,945 discussed a hydraulic, radiopaque paste containing a hygroscopic clay and calcium chloride, but not a calcium aluminate cement or glycol such as mentioned herein. Hygroscopic clays expand as they absorb fluid, and swelling can be problematic in dentistry because of the potential to fracture teeth under "hoop stress". A hygroscopic clay is not used in the present invention.

Kraft and Hermansson (U.S. Pat. No. 6,620,232 B1, 1995) patented a calcium aluminate cement that may include calcium silicate cement, but the preferred amount was 1 to 5 volume percent, not the roughly equal amounts of calcium aluminate and calcium silicate cement used herein. Pandolfelli et. al. disclosed a calcium aluminate material in US 2011/0281241 (2011); however, it did not include calcium silicate cement or provide any motivation to use it.

Frenkenberger et al. in U.S. Pat. No. 8,545,620 (2013) invented a cement designed to quickly set at cold temperatures comprising calcium silicate and calcium aluminate cements, with a trifunctional polyalkylene glycol. In the present invention, the amount of calcium aluminate is higher in proportion to the calcium silicate disclosed in Frenkenberger, and glycol is optional. Engqvist et al. in U.S. Pat. No. 9,676,665 B2 (2017) mentioned combinations of calcium silicate and aluminate cements composition with non-aqueous liquids, but in addition Engqvist compositions contain calcium phosphate compositions, which are not included in the present invention. Engqvist also emphasizes refrigeration for paste preservation, which is also not required herein.

SUMMARY OF THE INVENTION

The technical problem with existing materials is they do not combine all the characteristics that are needed by medical professionals in specialized dental and medical biomedical cements. The present invention has industrial applicability and fulfills a continuing need. The features, versatility, and advantages of the present invention include bioactivity, biocompatibility, fast setting, self-hardening into a dense and strong material as a result of the hydraulic setting, easy placement, resistance to washout, resistance to acids for better performance where infection is present, an adequate (at least one year and preferably two years and most preferably three years) shelf life, and non-exothermic setting reaction. Significantly, the setting reaction is neither expansive nor contractive, which is a highly desirable property for a cement used for the fixation of devices or filling of body cavities with a cement.

Bioactivity is a desirable feature of some ceramic materials, including calcium phosphates, calcium hydroxide, bioactive glasses, tri/dicalcium silicate cements, and calcium aluminate cements. Bioactivity means the body will form hydroxyapatite on the surface of the material. The hydroxyapatite effectively shields the material from the body to reduce foreign body reactions. Bioactive ceramics are highly alkaline, pH >10, and release calcium ions. The high pH at the surface of the ceramic will induce the calcium ions to react with the phosphate ions in physiological body fluids surface to precipitate a calcium phosphate phase that resembles calcium deficient hydroxyapatite, the mineral in bone, dentin and enamel. The same effect is observed in synthetic body fluids, and used as a way to determine bioactivity in vitro [Ref 6, ISO23317]. This surficial layer of hydroxyapatite hides the underlying cement from the body to minimize cytotoxicity and inflammatory responses to promote healing. The release of calcium ions will activate healing reactions by the cells, such as formation of new bone cells over the cement. Distinct advantages accrue to self-setting materials, including the present invention, over calcium hydroxide alone.

Two classes of hydraulic (water-setting) ceramic cements are known to be self-setting and bioactive: calcium silicate cements and calcium aluminate cements. The present invention comprises both. The common cement-forming compositions for each are represented in the accompanying ternary ceramic phase diagram for calcia, alumina and silica. Calcium silicate or calcium aluminate cements can be manufactured over small ranges of compositions including all three oxide components; however, the compositional ranges for the cements do not overlap (as observed in the sole diagram accompanying this invention disclosure). Calcium aluminate cements and calcium silicate cements must be manufactured separately to achieve the desired hydraulic phases shown in the ceramic phase diagram; otherwise, non-hydraulic phases may be formed such as calcium silicate ($CaSiO_3$), gehlenite $Ca_2Al(AlSiO)_7$ and lime (CaO). The tricalcium aluminate phase is hydraulic but reacts very rapidly with water at an impractical rate, therefore acceptable as a part of the present invention only in minor quantities.

Calcium aluminate and calcium silicate cements are manufactured by intimately mixing calcia, silica, and alumina-containing powders and then firing such mixtures to a high enough temperature to react and form the compounds shown in the accompanying ceramic phase diagram. The firing process for calcium silicate cements forms tricalcium silicate ($Ca_3SiO_5$, $C_3S$) and usually dicalcium silicate ($2CaO \cdot SiO_2$, $C_2S$). Minor amounts of tricalcium aluminate phase ($3CaO \cdot Al_2O_3$, $C_3A$) or tetra calcium aluminoferrite ($4CaO \cdot Al_2O_3Fe_2O_3$, $C_4AF$) may be formed, depending on the raw materials. Iron oxide may be included intentionally or as a minor component of raw materials, which commonly reduces the firing temperature required. Firing calcia and alumina with minor amounts of silica will form predominantly calcium monoaluminate (CA), calcium aluminate cement. After firing, each cement is ground into a fine powder so that it has a large surface area to react with water. A finer ceramic powder is of value for mechanical interlocking in trabecular bone or dentinal tubules. Penetration of the bone or dentin will enhance the adhesion and strengthening where the cement is placed and can exert local antimicrobial or bioactive effects, and desirably facilitate the formation of hydroxyapatite on the complex surfaces of the set cement within the body.

Calcium silicate cements are ubiquitous in the built environment. Calcium sulfate is commonly blended with the tri/dicalcium silicates to control and slow the setting reaction for construction projects.

Calcium aluminate powders are primarily used for industrial application as refractory cement that is heated to very high temperatures during use. Structural use of the calcium aluminate cements is hindered by "conversion reactions". From 10 to 27° C. the hydration reactions of calcium aluminate cement hydrate and form $CaO \cdot Al_2O_3 \cdot 10 H_2O$. Above 27° C., for instance at body temperature, hydration forms $2CaO \cdot Al_2O_3 \cdot 8H_2O$. If $CaO \cdot Al_2O_3 \cdot 10 H_2O$ is formed first, this hydrated phase can convert at higher temperature to $2CaO \cdot Al_2O_3 \cdot 8H_2O$ and release $2Al(OH)_3$ and water. Conversion reactions increase porosity in the calcium aluminate cements by release of the water, which decreases its strength. However, such reactions occur when such cements are used at changing temperatures, unlike what occurs when a material is placed in a body which maintains a relatively constant temperature.

In spite of the potential for conversion, calcium aluminate cements are known for their good resistance to chemical attack. These cements and have been used to mitigate sewer corrosion (by sulfuric acid) in place of calcium silicate-type (Portland) cement. Additionally, the calcium aluminate cements are more durable in seawater, a substance akin to physiological body fluids. Bodily infections create an acidic environment, therefore calcium aluminate in cements were imagined to be beneficial for setting in vivo where infection is present. Thus, the calcium aluminate component of the present invention has the advantage of enhanced resistance to acidic conditions over calcium silicate cements, such as those disclosed hereinabove for the prior art inventions of Torabinejad ('547 and '638), Primus ('342), or Lu and Zhou (U.S. Pat. No. 7,553,362, 2009).

The setting times for construction grade Portland (tri/dicalcium silicate) or calcium aluminate cements are usually much longer than desired for medical or dental applications, where setting within minutes is useful. Although long setting times are desirable for larger-scale industrial applications, different compositions and properties are needed for biomedical applications. The combination of the two calcium cements is known to lead to a shorter setting time [Ref 7, Tan et. al], although not as brief as in the present invention.

For medical cements, the raw materials must be of high purity, unlike construction-grade Portland cement and exclude traces of lead and arsenic, and preferably exclude also cadmium, tellurium and antimony.

Silica is considered an essential mineral for bone formation [Ref 8, Carlisle]. Hence, the two hydraulic bioactive ceramic cements were combined in the present invention to achieve combined medical benefits of acid resistance, faster setting, bioactivity, and silica availability for osteogenic purposes to assist bone or dentin repair.

An ideal biomedical cement will have the following characteristics with some variation depending on the indication: biocompatible (non-cytotoxic at least after setting, non-irritating, non-sensitizing, non-allergenic, and non-mutagenic), bioactive [including elevated pH and calcium ion release] (or at least bioinert), antibacterial or bacteriostatic, radiopacity, minimal shrinkage or expansion, hydrophilicity to be unaffected by moisture or blood, setting and working times suitable for procedure (ranging from a few to about 30 minutes) at room and body temperature, easy to manipulate and place, washout resistant, low heat of setting, low contact angle with tissues, sets under infected conditions that are acidic, will enter dentinal tubules or trabecular bone spaces for mechanical adhesion, promote cementogenesis and regeneration of bone and periodontal ligament, seal a site hermetically, adhere to surrounding tissue, include fine particles (if non-soluble), radiopacity, dimensionally stable, non-discoloring, having a bone or tooth-like color that does not change over time, and be cost-effective. The present invention is designed to meet all these criteria, and examples below demonstrate most of these characteristics. Some characteristics may depend on the intended use such as: format for preparation such as mixing, viscosity, porosity, resorbability and impermeability. The present invention has the versatility to be suitable for a wide variety of clinician requirements unlike much of the prior art.

A solution to the problems of acid resistance, quick-setting, with biocompatibility and bioactivity has been found in the present invention which includes the combination of two, fine, ceramic hydraulic cements with unique characteristics unlike other biomedical cement inventions in use today. Combining primarily calcium silicate and calcium aluminate hydraulic cements, even with the further inclusion of a radiopaque powder, provides for faster setting in vivo and enhanced resistance to acids than can be achieved with calcium silicate cement alone.

This present invention also has versatility in its preparation, delivery and use. The cement powder may be inserted with an instrument into the body for setting through interaction with the body fluids. The cement powder may also be supplied separate from, but with either a water or a water-based liquid added and mixed with it just before use. The present invention cement powder may also be supplied in a capsule that is activated to combine the powder and liquid just before use. The present invention cement powder can also be mixed with a non-aqueous liquid into a ready-to-use paste, which will set by interaction with the body liquids. Another present invention embodiment is characterized by the hydraulic and non-hydraulic components of the bioactive ceramic cement being separately blended with liquids and the pastes are combined just before use.

It is an object of the invention to provide a bioactive ceramic cement for use in mammals based on at least two calcia, alumina, and silica-containing powdered hydraulic compounds that has a suitable setting time for use in fixation of bones or devices in the body, filling of body cavities, including dental needs, that features radiopacity, ability to set in vivo, avoids displacement from its in vivo locations by irrigation with water or bodily fluids, and is more suitable for oral supragingival use than is possible with the current prior art.

The advantageous effects of the invention are its combination of hydraulic ceramic phases that create a fast-setting, dimensionally stable, bioactive, and biocompatible cement which has enhanced performance in in vivo applications. The versatility of the present biomedical ceramic cement invention for various delivery conditions and indications is of value to clinicians.

BRIEF DESCRIPTION OF THE DRAWINGS

The sole illustration accompanying this disclosure is a simplified ceramic phase diagram adapted to show non-overlapping regions for Calcia, Alumina, and Silica where calcium silicate and calcium aluminate cements are stable. It was adapted from a more complex diagram used by Leif Hermansson whose publication is entitled: A Review of Nanostructured Ca-aluminate Based Biomaterials within Odontology and Orthopedics, Journal of the Korean Ceramic Society 2018; 55(2): 95-107. Visually, the cement phases used in the present invention are shown in this sole illustration where area 1 indicates the calcium silicate cement region and area 2 indicates the calcium aluminate cement region. It is important to note that these formula regions 1 and 2 are non-overlapping and distinct from one another.

DESCRIPTION OF EMBODIMENTS

Examples

The present disclosure of a hydraulic bioactive medical ceramic cement material herein includes a fine ceramic powder component, which is a combination of hydraulic cement powders. The hydraulic powders used in the present invention are distinctively different and involve the combination of hydraulic ceramic compounds: monocalcium aluminate cement, tricalcium silicate and dicalcium silicate. Such a ceramic powder component, further combined with radiopaque powders and other minor ingredients creates a versatile bioactive medical ceramic cement. This present invention material may be used to create a variety of products of low and high-viscosity; (such as 100K cP and 2,500K cP) that can also set in vivo and be bioactive.

The generally accepted composition ranges for the two ceramic cements depicted in the sole illustration accompanying this invention disclosure are listed in Table 1 by chemical components and in Table 2 by phases. The phases present in calcium silicate hydraulic materials differ from those present in calcium aluminate powder.

TABLE 1

Comparisons of Hydraulic Cement Compositions

| Component | Cement notation | Calcium silicate Minimum | Calcium silicate Maximum | Calcium aluminate Minimum | Calcium aluminate Maximum |
|---|---|---|---|---|---|
| CaO | C | 61 | 67 | 17 | 33 |
| $Al_2O_3$ | A | 2.5 | 6 | 65 | 81 |
| $Na_2O$ | N | 0 | 0.3 | 0 | 0.6 |
| $SiO_2$ | S | 19 | 23 | 0 | 0.8 |
| $Fe_2O_3$ | F | 0 | 6 | 0 | 0.4 |
| MgO | M | 0 | 0.4 | 0 | 0.4 |
| Sulfate | | 1.5 | 4.5 | 0 | 0 |

TABLE 2

Phase composition (weight %) of Hydraulic Cements

| Clinker | Cement notation | Calcium silicate | Calcium aluminate |
|---|---|---|---|
| Tricalcium silicate $(CaO)_3·SiO_2$ (alite) | $C_3S$ | 45-75 | 0 |
| Dicalcium silicate $(CaO)_2·SiO_2$ (belite) | $C_2S$ | 7-32 | 0-7 |
| Tricalcium aluminate $(CaO)_3·Al_2O_3$ | $C_3A$ | 0-13 | 0 |
| Tetracalcium aluminoferrite | $C_4AF$ | 0-18 | 0 |
| Gypsum $CaSO_4·2\ H_2O$ | | 2-10 | 0 |
| Monocalcium aluminate $CaAl_2O_4$ | CA | 0 | 35-70 |
| Dodecacalcium heptaaluminate | $C_{12}A_7$ | 0 | 0-10 |
| Monocalcium dialuminate $CaAl_4O_7$ | $CA_2$ | 0 | 0-30 |
| Alumina $Al_2O_3$ | A | 0 | 0-33 |
| Gehlenite $Ca_2Al[AlSiO_7]$ | $C_2AS$ | 0 | 1-11 |
| Wüstite (FeO) | F | 0 | 0-7 |

A prior invention disclosure of the applicant/inventor herein, (Primus '342) mentioned the use of calcium aluminate and calcium silicate cement. Although calcium monoaluminate cement was mentioned, the examples only included tricalcium aluminate cement. Also, the final setting time in Primus '342 was noted to be about 2 hours for a combined cement, but not the 2 to 5 minutes for the initial setting time disclosed herein for the present invention; wherein, the setting time is variable depending on the powder-to-water ratio.

Calcium aluminate and calcium silicate cements are combined in the present invention to improve acid resistance and set faster. The combination also lowers the pH slightly, while remaining alkaline, which may reduce inflammation or cytotoxicity in contact with tissue, yet retain the bioactivity of cement to support healing responses. The acid resistance of the calcium aluminate cement may enhance the setting of these bioactive cements in the presence of infections encountered when placed in perforations in root walls or infected root tips. Faster setting is appreciated by medical professionals. The combination of ceramics providing the matrix of the present invention is useful because bone regeneration is assisted by the presence of silica, with reduced vulnerability to acid.

Ceramic cements for industrial uses with a low price are preferred, and are achieved by manufacture with less grinding, creating a coarser particle size. In medical devices, a fine powder is preferred. The particle size of the powder used as a part of the present invention is substantially reduced. Preferably, any auxiliary powders are as fine or finer than the ceramic cement powders, and may contain nanoparticles (<0.1 μm, 100 nm).

The components of powders in the present invention products (both cement and auxiliary powders) are all fine powders with a maximum particle size less than 20 μm and preferably less than 15 μm with a median particle size less than 9 μm and preferably less than 5 μm, and additionally with up to 10% nanoparticles. The fineness of the powder importantly increases the surface area, which increases the reactivity and speed of present invention setting, enables its penetration into bone or tooth architecture, makes dispensing of the present invention possible through 30-gauge syringe tips, reduces segregation of powder and liquid, and makes present invention pastes more homogeneous with a smooth feel to the paste.

The fineness of the present invention powders should include its radiopaque powder, which may include those compounds mentioned below. However, bismuth compounds are avoided because of the multiple oxidation states of bismuth that have colors ranging from yellow to dark brown. Oxidation of bismuth compounds are known to occur in the presence of formalin, sodium hypochlorite, and when exposed to light. Discoloration of prior inventions, such as Torabinejad '547 and '638, and Primus '342, has been observed when used within the primary teeth having thin enamel layers [Ref 9, Hutcheson]. Without the use of bismuth, discoloration of the present invention is avoided in dental applications. Many other ceramic or metal compounds provide radiopacity and are inert.

The powder formulas 1 through 6 in Table 3 are examples of bioactive ceramic cement powders contemplated by the present invention herein. These powders can be mixed with any water-based liquid and set, but were also mixed with a non-aqueous liquid noted in Table 4 to make pastes. The pastes in Table 4 are created for the convenience of the dentist or other medical professional to dispense without mixing. As the pastes set in vivo, the organic liquid is replaced by water from the body fluids to set the hydraulic cements. The powders hydrate and remain in the tooth as a hard mass; the organic liquid diffuses out of the treated area.

One example of a bioactive cement according to the present invention contains 40% tantalum oxide, 25% of a calcium aluminate cement, 25% calcium silicate cements, 9% of a fluidic stabilizing component and 1% of a salt. The fluidic stabilizing component may be inorganic or organic and include zeolite, chitosan, xanthan gum, polyacrylic acid, sodium polyacrylate, calcium lactate gluconate, and non-expansive clays. The fluidic stabilizing components create a dense cohesive paste when a liquid is mixed with the powder, and minimize the segregation of the fine powder and the liquid in bulk or in containers. Naturally occurring, water-soluble polymers which are preferred as a part of the present invention, but not limited thereto, include guar gum, pectin, xanthan gum, chitosan and its derivatives, carrageenan, cellulose ethers, hyaluronic acid (HA), albumin, and starch. Depending on the concentration, some of these polymers, such as polyacrylic acid and sodium polyacrylate have been blended with the ceramic powder for dissolution when a water-based liquid is added to the powder.

Many salts have been used to accelerate or retard the setting of calcium silicate cements [Ref 10, Taylor]. Salts have been included to reduce the foaming of the cement when it is mixed with liquids and may also accelerate the setting. Salts suitable for this invention include sodium carbonate, potassium carbonate, calcium nitrate and lithium nitrate.

Some polymers may be added to the present invention to introduce a slight expansion by being superabsorbent, that is absorbent of water or tissue fluids, and imparting a slight expansive characteristic. This expansion may be useful for filling the complex anatomy where the cement is placed, providing more interlocking of the cement and bone or tooth. Slight expansion is beneficial compared to polymerization shrinkage.

When a bioactive scaffold is needed, salts or polymeric additives that cause foaming may be added to cement mixtures. Foamed cements have been made for other industrial application such as U.S. Pat. No. 3,926,650 A (Lang et. al, 1975). A permeable cement may be suitable to fill a bone void with a porous material that can then be infiltrated by cells over time [Ref 11, Zhang et. al] and is disclosed in U.S. Pat. No. 5,149,368 (Liu et. al, 1992). Cells may resorb normally non-resorbable materials if porous. Other powders enhance resorption including a bioactive glass or calcium sulfate which are resorbable components that can create pathways for tissue engineering and cell in-growth in the cement as the additives are resorbed. Salts that cause foaming may also be used with the present invention for the same or similar purposes.

A preferred example of a bioactive cement, identified by the number 6 in Table 3 herein below, shows the present invention containing 25% of a calcium aluminate cement, 25% calcium silicate cement, 40% tantalum oxide, and 6% of a fluidic stabilizing component by weight.

TABLE 3

Example of Compositions of Bioactive Ceramic Cements (weight %)

| Powder Component | 1 | 2 | 3 | 4 | 5 | 6 | 7 |
|---|---|---|---|---|---|---|---|
| Tri/dicalcium silicate cement | 30 | 24 | 24 | 24 | 23 | 25 | 24 |
| Calcium aluminate cement | 35 | 24 | 24 | 24 | 23 | 25 | 24 |
| Radiopaque component: tantalite, calcium tungstate or zirconia | 35 | 46 | 46 | 46 | 45 | 40 | 46 |
| Halloysite | | | 6 | | | 9 | |
| Xanthan gum | | | | 6 | 9 | | |
| Zeolite | | 6 | | | | | |
| Sodium carbonate | | | | | | 1 | |
| Water-soluble polymer | | | | | | | 6 |

The combination of calcium aluminate and calcium silicate cements in this preferred example of bioactive cement 6 reduced the initial setting time. The initial setting time is important to clinicians because they want to be sure the material is stably placed at the site, rinse the site, and close the opening. As a result, the present invention herein provides compositions wherein a certain degree of firmness can be developed at various times after mixing. The ceramic cement powder mixed with water at a ratio of 3:1 by weight has an initial set in 3 minutes, which is desirable in dentistry. In this configuration, the calcium silicate content is less than 20%.

The radiopaque component of the present invention may be any combination, but not limited to, the following powders: barium sulfate, calcium tungstate, cerium oxide, gold, iodoform, phosphate-based glass, silver, silicate glass, tantalum oxide, tungsten, zinc oxide, or zirconia. Any glass powder should contain baria or strontia for radiopacity. Usually the amount of radiopaque agent is kept to less than 60 weight percent and less than 50 mole percent, which is always less than the weight percent. The radiopacifier may have multiple purposes such as enhanced radiopacity, providing an antimicrobial effect, or contributing a color.

The ceramic powders of Table 3 can be inserted in the body to self-set in the presence of body fluids. Instruments for powder placement include but are not limited to a Dovgan carrier, an endo gun, a MAP system, or an amalgam carrier.

Alternatively, the biomedical cements of the present invention can be mixed with various liquids, water-based and non-aqueous, prepared at various consistencies, low or high viscosity, to harden and create a bioactive ceramic cement in vivo. This versatility is useful clinically. For instance, a material intended for bone fragment fixation or root-end filling requires a higher powder to liquid ratio and preferably a more viscous gel for a more putty-like consistency than one would need for cementing a tooth implant, an endodontic post or for a root canal sealer, which are desirably more fluid. The consistency of the present invention can range from a thin injectable paste that can be delivered through a 30-gauge or larger needle, to a thick clay-like consistency, depending on the preparation of the cement powder with liquid as a paste.

The present invention bioactive cement may be supplied with a separate container of liquid for mixing just before use. The simplest liquid that can be combined with a powder phase to form the present invention is water. This leads to a very fast setting cement, about 3 minutes, using a Gilmore needle apparatus per the ISO 6876:2012 (Endodontic Sealing Materials) method.

A water-based liquid may be supplied with present invention ceramic powder that includes various salts. Certain additives are known to accelerate or retard the setting of calcium cements and can be added to the ceramic cement powder or to an accompanying liquid. Accelerants may preferably include, but are not limited to: lithium salts, calcium hydroxide, potassium hydroxide or carbonate, potassium carbonate, and sodium hydroxide, carbonate, or sulfate. Other inorganic compounds may have a retarding effect [Ref 12, Lea] on setting.

A water-based liquid for the present invention ceramic cement may include organic water-miscible liquids, silica solutions, or water-soluble polymers. When mixed or dissolved in water, these additives can improve the handling and manipulation of the cement for the convenience of the clinician. The organic liquids may include glycerin, glycols, and fish or vegetable oils. Water-soluble synthetic polymers may include polyvinyl alcohol (PVA), polyvinyl pyrrolidone (PVP), polyethylene glycol (PEG), polyacrylic acid (PAA), polyacrylamides, N-(2-Hydroxypropyl) methacrylamide (HPMA), DIVinyl Ether-Maleic Anhydride (DIVEMA), polyoxazoline, polyphosphates, and polyphosphazenes. Such water-miscible liquids, solutions or water-soluble polymers may be included in a liquid to mix with the powder to create special features of flow, film thickness, working or setting time. A liquid to accompany the present invention cement may comprise naturally occurring, water-soluble polymers, including but not limited to guar gum, pectin, xanthan gum, chitosan and its derivatives, carrageenan, cellulose ethers, hyaluronic acid (HA), albumin, and starch. These liquids must be stable and not contain bioburden.

The molecular weight of the water-soluble polymers in gel form for use with the present invention bioactive cement may be selected to pinpoint the desired viscosity of the cement after mixing with a liquid. Higher molecular weights make more viscous solutions requiring less polymer and can be used to create a porous cement when set. The powder, when rapidly spatulated with viscous liquid can create a foamy material for implantation with bubbles that remain after setting. Such a porous structure may be suitable for resorption over time, such as required in bone replacement. Ideally, the bubble size should be on the scale of the bone site, greater than 100 μm with interconnected porosity [Ref [13], Petrochenko]. The opposite is true for the lower molecular weight polymers. The lower molecular weight polymers lead to lower viscosity liquids that are less likely to form bubbles. High and low molecular weight polymers can be mixed and combined for use as a part of the present invention, including but not limited to polyvinyl alcohol, polyvinyl pyrrolidone, polyethylene glycol (PEG), polyacrylic acid (PAA), polyacrylamides, N-(2-Hydroxypropyl) methacrylamide (HPMA), DIVinyl Ether-Maleic Anhydride (DIVEMA), polyoxazoline, polyphosphates, and polyphosphazenes.

A low-viscosity liquid (less than 50,000 cP) that creates a long working time for the present invention bioactive cement and a highly elastic mixture will preferably contain <10% low volatility organic liquid, <5% of a defoaming salt or other material, <50% of a water soluble polymer of low molecular weight and water. The powder and liquid will be mixed at a ratio from 2:1 to 1:1, depending on the clinical preference.

A high-viscosity gel can be mixed to offer a shorter working time for the present invention bioactive cement and a clay-like consistency of the mixture, which will preferably contain <30% low volatility organic liquid, <50% water-soluble polymer, <5% of a defoaming salt, and water. Such water-soluble polymers may be a mixture of low, medium and high molecular weights. The powder and gel will be mixed at a ratio from 4:1 to 2:1, depending on the clinical preference.

Any of the liquids can be combined with the present invention bioactive cement in a capsule and mixed mechanically as in U.S. Pat. No. 5,394,980 (1995 Tsai). Alternatively, the powder and liquid can be packaged in a mixing syringe that is useful for the self-mixing therein, as in U.S. Pat. No. 8,454,558 B2 (2013 N. Jessop, et. al.). The powder and liquid can be packaged in a 2-compartment foil pouch and the barrier removed between the compartments for mixing just before use.

Unitary pastes having a long shelf life, >1 year shelf life, can be created with present invention bioactive ceramic cements. Such pastes set more slowly than the powder-water mixtures, but faster than other pastes based on only tri/dicalcium silicate cement. The bioactive powder of this invention may be blended with a non-aqueous liquid such as a glycerin or other organic liquids to create a biocompatible bioactive unitary paste. If the amount of liquid blended with the powder is about 60 to 75%, a low-viscosity paste (<50,000 cP) is formed that can be injected into a body cavity. In dentistry, such a paste would be useful for cementation of a prosthetic device, vertebral surgery, or non-surgical endodontic therapy using gutta percha points to obturate a root canal. If the powder percent is increased from 75 to about 85% powder, a high-viscosity (>500,000 cP), clay-like paste is created that can be used to pack into voids, and occlude openings in teeth either apically or coronally. Optionally, polymers may be dissolved in the non-aqueous liquid to adjust the setting time, viscosity, flow, or elasticity of the paste. Non-aqueous liquids are mixed with the ceramic powder to ensure a long-shelf life of the paste; otherwise the cement would quickly set.

TABLE 4

Examples of Bioactive Paste Compositions (weight %)

| | High-viscosity paste, clay-like Viscosity~1,000,000 cP | | | | Low-viscosity paste Viscosity~200,000 cP | | | |
|---|---|---|---|---|---|---|---|---|
| Pastes # → | 8 | 9 | 10 | 11 | 12 | 13 | 14 | 15 |
| Tantalite or zirconia | 35.9 | 35.9 | 35.9 | 35.1 | 31.3 | 31.3 | 31.3 | 30.6 |
| Tri/dicalcium silicate | 18.7 | 18.7 | 18.7 | 17.9 | 16.3 | 16.3 | 16.3 | 15.6 |
| Calcium monoaluminate | 18.7 | 18.7 | 18.7 | 17.9 | 16.3 | 16.3 | 16.3 | 15.6 |
| Zeolite | 4.7 | 0.0 | 0.0 | 0.0 | 4.1 | 0.0 | 0.0 | 0.0 |
| Nano-clay | 0.0 | 4.7 | 0.0 | 0.0 | 0.0 | 4.1 | 0.0 | 0.0 |
| Xanthan gum | 0.0 | 0.0 | 4.7 | 7.0 | 0.0 | 0.0 | 4.1 | 6.1 |
| Water miscible organic liquid | 22.0 | 22.0 | 22.0 | 22.0 | 32.0 | 32.0 | 32.0 | 32.0 |
| TOTAL | 100.0 | 100.0 | 100.0 | 100.0 | 100.0 | 100.0 | 100.0 | 100.0 |

The choice of liquid for making a unitary paste affects the shelf life of the paste. For instance, a commercial dental paste that contains tri- and dicalcium silicate but no alumina phase was compared to a high-viscosity unitary paste of the present invention. Both pastes were placed in small polytetrafluoroethylene molds at 37° C. and ambient humidity. The commercial paste had a shorter time before initial setting, 8 days, whereas the paste of the present invention did not undergo initial setting after 14 days. A longer working time, such as measured, is indicative of longer shelf life, with less evaporation of the organic liquid and less susceptibility to humidity.

A high-viscosity unitary paste was made of the present bioactive powder invention and compared to a commercial dental paste that contains no alumina phase but does contain tri/dicalcium silicate powder. Both the commercial and the paste of the present invention were placed in small polytetrafluoroethylene molds at 37° C. in a high humidity environment. The commercial paste did not set in 30 hours whereas the bioactive putty set initially in about 2:45 hr. and the final set was less than 9 hours. Although the setting time is significant for both materials, the complete setting is important to impart strength and sooner is better for healing. Therefore, the present invention has an apparent longer shelf life, but shorter setting time than other inventions.

The bioactive cement of this invention may be provided as a thick unitary paste in a syringe, with a second bottle or syringe of liquid. The clinician would dispense paste and if desired, add some of the supplied diluent liquid to reduce the viscosity just before use. If the diluent liquid is a water-based liquid, the mixed paste can begin to set immediately. If the diluent liquid is a non-aqueous liquid, the mixed paste, will have a longer working time and start setting when placed in vivo.

The bioactive medical ceramic cement powder of the present invention may be provided as multiple pastes, and the multiple pastes must be combined just before use. For instance, the radiopaque component may be combined with a water-based liquid in a paste in one syringe. The cement may be mixed with a non-aqueous liquid as a paste in a second syringe. The clinician would dispense paste from the two syringes, preferably in equal volumes, and mix the pastes just before use. Alternatively, the radiopaque component may be suspended in a water-based liquid and when mixed with the cement paste, the mixture may begin setting. If the radiopaque component is suspended in a non-aqueous liquid, the mixed paste from the two syringes will have a longer working time and start to set in vivo. The pastes may be packaged in two separate tubes or syringes, or the pastes can be packaged in a dual-barreled syringe and dispensed together by a common plunger, through a spiral, static mixing tip, which eliminates hand mixing.

Alternatively, the present invention of bioactive powder may be provided as more than two pastes, and the multiple pastes must be combined just before use. For instance, the radiopaque component may be combined with a non-aqueous liquid in one syringe as a very viscous paste. The present invention cement may be mixed with a non-aqueous liquid in a second syringe as a viscous paste. A third syringe or bottle containing a water-based gel may be combined with the other two pastes just before use to the viscosity desired. The combination of the three items would begin setting when mixed. Non-aqueous liquids ensure a long-shelf life of the cement-containing paste.

When a present invention low-viscosity bioactive cement mixture is manufactured, the ceramic medical cement can meet the requirements of international standards for dental materials, including those for endodontic sealers (ISO 6876: 2012): flow greater than 17 mm, film thickness less than 50 µm, solubility less than 3%, and radiopacity more than 3 mm of equivalent aluminum. The dimensional stability of the cement is less than 0.1% expansion, and shrinkage less than 1% as required in ADA 57. The compressive strength after 28 days exceeds 35 MPa required in ADA 30:2013 for zinc oxide-eugenol for temporary cements, and the arsenic and lead contents are less than 2 and 100 ppm as required in ISO 9917-1 for water-based cements.

When powders, gels and pastes are made according to the present invention, the resulting material has enhanced properties over that of U.S. Pat. No. 7,892,342 B2 (Primus, 2011) as noted in Table 5. Furthermore, the resistance to washout is far superior compared to U.S. Pat. No. 7,892,342 B2 material. The pH is slightly lower, which contributed to the better biocompatibility with cells. The radiopacity was higher with more ceramic radiopaque powder.

TABLE 5

Physical Properties of Hydraulic Materials for Medical and Dental Uses

| Material | Initial Setting Time (hr:mm) | Radiopacity (mm of Al) | Film thickness (μm) | Loss after Washout (weight %) | Dimensional stability (% linear change) |
|---|---|---|---|---|---|
| Present Invention as unitary pastes (low and high-viscosity) | 3:50 to 2:20 | 7.0 to 8.2 | 35 to 380 | 18 | <0.2% |
| Present invention as powder & water (2:1) | 0:03 | 7.2 | 350 | Not tested | <0.1% |
| Material of Primus '342 | 2:55 | 5.0 | 350 | 100 | <0.1% |

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited in this disclosure and in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Although examples of the inventive compositions have been provided in the foregoing detailed descriptions, it should be understood that the invention is not limited only to the examples disclosed, but is intended to embrace any alternative, equivalent, modification, or rearrangement falling within the scope of the invention as defined by the following claims.

INDUSTRIAL APPLICABILITY

Industrially, a medical device may be manufactured using the present invention that is convenient, advantageous, and efficacious. The benefits include bioactivity, self-setting, biocompatibility, high pH, antimicrobial, improved acid resistance, faster setting, long life for premixed paste. This combination of features provides distinct and important advancement in the field.

The bioactive cement may be manufactured in a variety of versatile configurations and formats to address various needs for medical devices and supplied as kits to a clinician. One option is that the powder may be supplied alone. In vivo, the body fluids will be absorbed by the powder and setting will occur.

Another option is that the present invention bioactive ceramic cement may be provided as a two-part system with powder and water, or powder and a water-based liquid.

Furthermore, the present invention bioactive powder and a liquid may be packaged together in a capsule similar to capsules used for dispensing a unit-dose of dental amalgam such as shown in U.S. Pat. No. 5,394,980 (Tsai, 1995). In this capsule format, a barrier is used between the powder and liquid that is perforated just before use. After the barrier is broken powder and liquid can be mixed in a triturator, or dispensed for final mixing by hand. Alternatively, a capsule can be used for the present invention powder. Just before use, the capsule can be opened and liquid can be added to the powder in the capsule. The powder and liquid can be triturated in the capsule and then dispensed for placement.

Alternatively, a two-part foil pouch may be used with the present invention powder on one side and the liquid on the other. When a barrier is breached between the compartments, the powder and liquid can be mixed by hand in the pouch and then squeezed to dispense for placement in vivo.

Each of the formats has its own advantages depending on the indications for the clinical situations. For instance, a thick paste is especially suitable for in dental root-end filling and pediatric pulpotomy treatments, since time is especially important for treating children or in a root-end surgical operation. A thinner paste is needed for bone cement or root canal sealing with gutta percha. A paste with an intermediate viscosity is useful for filling uniting or aligning fractured bones or for placement of implants or an endodontic post.

The present invention ceramic medical cement can be used for permanent implantation with soft or hard tissue contact, particularly bone, pulpal or periradicular (root/bone) tissue. Resorption will not occur for the bioactive cement after setting, unless a foaming agent is used or if the material is mixed to such a thin consistency it would not set. The invention herein is suitable for use in the presence of blood or bodily fluids as the material is hydrophilic and sets in the presence of blood or fluid.

As described, the ceramic medical cement powder disclosed herein can be prepared in a variety of formats, but the powder is always biocompatible and bioactive when set because the setting reaction is the same: hydration of the two cement components forming a high pH cement that will elute calcium and hydroxide ions in water.

A benefit of the present invention cements is the dimensional stability of the ceramic materials after reaction with water. Neither shrinkage or expansion occurs. As a result the cement meets the ADA 57 standard for endodontic sealing materials of less than 1% linear shrinkage and less than 0.1% linear expansion. The dimensional stability is unlike polymers that generally shrink several percent and could allow bacteria ingress through the passage created by shrinkage. Expansion would also be deleterious as a material could create a hoop stress within the canal and fracture the root.

In dentistry, early childhood caries is a worldwide epidemic, and a global increase exists in dental caries prevalence in adults' permanent teeth. Performing pulpotomy treatment for deep caries is important for the primary teeth because caries are painful and interfere with nutritional intake. Furthermore, the premature loss of a tooth affects jaw bone development, speech, and the development and eruption of permanent teeth. Maintaining the vitality of the remaining pulp, after a pulpotomy, is especially important for immature, incompletely developed teeth in young adults. Enabling the roots of developing teeth to lengthen and the walls of the roots to thicken will provide a lifelong benefit. In adults, the preservation of tooth vitality via a pulpotomy is the lowest cost and least invasive approach. Pulpal or other endodontic treatment is often required for trauma, and a bioactive medicament is preferred. Thus, there is a continuing need for new products, such as the present invention bioactive medical ceramic cement that is versatile in meeting a wide variety of clinician needs.

Similar growing needs exist for orthopedics as the population ages with concomitant osteoporosis and other bone trauma or atrophy.

The bioactive ceramic cement of the present invention has the following characteristics: biocompatible (non-cytotoxic after setting, non-irritating, non-sensitizing, non-allergenic, and non-mutagenic), bioactive, antimicrobial, radiopacity, minimal expansion (less than 0.1%) and fine particle size for sealing, unaffected by moisture or blood, short setting time as a powder with water but adjustable depending on the liquid, easy to manipulate and place, washout resistant when mixed with liquids described, low heat of setting, sets under acidic better than calcium silicate cement alone, non-discoloring, having a bone or tooth-like color that does not change over time, and cost-effective for maintaining teeth in vivo.

REFERENCE SIGNS LIST not applicable

REFERENCE TO DEPOSITED BIOLOGICAL MATERIALS not applicable

SEQUENCE LISTING/SEQUENCE LISTING FREE TEXT not applicable

CITATION LIST

Patent Literature

1. U.S. Pat. No. 3,926,650 A, Dec. 16, 1975, Lange J, Schneider G, Zeh A; Foaming agent for plaster and cement compositions.
2. U.S. Pat. No. 5,394,980 Mar. 7, 1995, Tsai H; Multicompartment mixing capsule.
3. U.S. Pat. No. 5,149,368 Sep. 22, 1992, Liu S-T, Chung H H; Resorbable bioactive phosphate containing cements.
4. U.S. Pat. No. 5,415,547 B1 May 16, 1995, Torabinejad M, White D J; Tooth filling and method of use.
5. U.S. Pat. No. 6,620,232 B1 Sep. 16, 2003, Kraft L, Hermansson L; Dimension stable binding agent systems for dental applications.
6. U.S. Pat. No. 5,769,638 B1 Jun. 23, 1998, Torabinejad M, White D J; Tooth filling and method of use.
7. U.S. Pat. No. 7,553,362 Jun. 30, 2009, Lu D, Zhou S. High strength biological cement composition and using the same.
8. U.S. Pat. No. 7,892,342 Feb. 22, 2011 Primus, C M; Dental material.
9. US20110281241 Nov. 17, 2011, Pandolfelli V C, Oliveira I R, Jacobovitz M, Rossetto H L; Aluminous composition for application in endodontics and cementitious product obtained thereof.
10. U.S. Pat. No. 8,454,558 B2 Jun. 4, 2013, Jessop N, McLean B S, Sheetz J; Syringe-in-syringe hollow inner barrel/plunger with integral seal and rupturable membrane and related kits, systems and methods.
11. U.S. Pat. No. 8,475,811 Jul. 2, 2003, Yang Q, Lu D, Premixed biological hydraulic cement paste composition and using the same.
12. U.S. Pat. No. 8,545,620 Oct. 1, 2013, Frenkenberger K, Kohler S, Heichele T, Hotzl K-D, Weiss P, Dressen A; Cement accelerator.
13. U.S. Pat. No. 8,658,712 Feb. 25, 2014; U.S. Pat. No. 9,801,792 B2 Oct. 31, 2017; U.S. Pat. No. 9,925,125 B2 Mar. 27, 2018 Primus C M, Gutmann J L, Breuer M M, and Jefferies S R; Methods of treatment of the dental pulp and filling root canals using water-based material.
14. U.S. Pat. No. 9,101,436 B2 Aug. 11, 2015 Chow L C, Takagi S; Dental and endodontic filling materials and methods.
15. U.S. Pat. No. 9,259,439 B2 Feb. 16, 2016, Chow L C, Takagi S; Dual-phase cement precursor systems for bone repair.
16. U.S. Pat. No. 9,676,665 B2 Jun. 13, 2017, Engqvist H, Aberg J; Storage stable premixed hydraulic cement compositions, cements, methods and articles.
17. U.S. Pat. No. 10,154,945 B2 Dec. 18, 2018, Jang S W, Lim H N, Kim E S, and Oh S J; Single paste type hydraulic dental filling composition.

Non Patent Literature

1 Vaishya R, Chauhan M, Vaish A. Bone Cement. J Clin Orthop Trauma (2013) 4(4): 157-63.
2 Fung M H T, Wong M C M, Lo E C M, Chu C H. Arresting Early Childhood Caries with Silver Diamine Fluoride-A Literature Review. Oral Hyg Health (2013)1:117.
3 Bagramian R A, Garcia-Godoy F, Volpe A R. The global increase in dental caries. A pending public health crisis. Am J Dent. (2009) 22(1):3-8.
4 Parirokh M, Torabinejad M. Mineral trioxide aggregate: a comprehensive literature review—Part I: chemical, physical, and antibacterial properties. J Endod. (2010) 36(1): 16-27; Mineral trioxide aggregate: a comprehensive literature review—part II: leakage and biocompatibility investigations. J Endod. (2010) 36(2):190-202; Mineral trioxide aggregate: a comprehensive literature review—Part III: Clinical applications, drawbacks, and mechanism of action.; J Endod. (2010); 36(3):400-13.
5 Primus C M, F, Niu L N, Bioactive tri/dicalcium silicate cements for treatment of pulpal and periapical tissues. Acta Biomaterialia (2019) 96(9):35-54.
6 ISO 23317, Implants for surgery—In vitro evaluation for apatite-forming ability of implant materials.
7 Tan Y, Liu Y, Birdi G, Grover L M, Li H, Li K. Calcium silicate/calcium aluminate composite biocement for bone restorative application: synthesis, characterisation and in vitro biocompatibility. Advances in Applied Ceramics (2016) 115(7):1-7.
8 E M Carlisle. Silicon: A requirement in bone formation independent of vitamin D1. Calcified Tissue International (1981) 33(1): 27-34.
9 Hutcheson C, Seale N S, Mcwhorter A, Kerins C, Wright J. Multi-surface Composite vs Stainless Steel Crown Restorations After Mineral Trioxide Aggregate Pulpotomy: A Randomized Controlled Trial, Pediatr Dent. (2012)34(7):460-7.
10 H. F. W. Taylor. Cement Chemistry, Thomas Telford (1997):323-338.
11 Zhang, J, Liu, W., Schnitzler, V, Tancret, F, Bouler, J-M, Review: Calcium Phosphate Cements (CPCs) for bone substitution: chemistry, handling and mechanical properties, Acta Biomaterialia (2014) 10(3): 1035-1049.
12 Lea's Chemistry of Cement and Concrete, 4th Edition, edited by Peter C. Hewlett (1998). 13 Petrochenko P, Narayan R J. Novel Approaches to Bone Grafting: Porosity, Bone Morphogenetic Proteins, Stem Cells, and the Periosteum, J Long Term Eff Med Implants. (2010)20(4): 303-315.

I claim:

1. A versatile biocompatible, osteogenic, bioactive, antimicrobial, and hydraulic self-setting ceramic cement composition for diverse medical, dental, and veterinary purposes, said ceramic cement composition characterized by;
   a fine ceramic cement powder having calcia, alumina, and silica compounds, that are hydraulic, including tricalcium silicate and monocalcium aluminate, said fine ceramic cement powder phase-having a maximum particle size less than 20 μm and a median particle size less than 9 μm;
   a fine radiopaque powder having a maximum particle size less than 20 μm, wherein when said fine ceramic cement powder is combined with said fine radiopaque powder to form a blended powder; and
   further wherein when said blended powder is in contact with at least one aqueous liquid, said blended powder begins to hydraulically set into a hardened cement mass while experiencing less than 0.1% dimensional expansion and dimensional shrinkage less than 1.0%, has increased resistance to acids present at the site where it applied over calcium silicate cement alone, has an inherent ability to form calcific layers in direct apposition to body tissue at the site where applied, and has a maximum initial setting time of 5 minutes at body temperature without raising the local temperature of the site where applied.

2. The ceramic cement composition of claim 1 also including at least one addition selected from a group consisting of dicalcium silicate, tricalcium aluminate, tetracalcium aluminoferrite, calcium silicate, monocalcium dialuminate, calcium oxide, silica, calcium sulfate, tricalcium disilicate, dodecacalcium hepta-aluminate, alumina, and monocalcium hexa-aluminate.

3. The ceramic cement composition of claim 1 further characterized by formulations in which said monocalcium aluminate is present within a range of 25% to 70% by weight for accelerated hydraulic setting into a hardened cement mass in teeth and bone for cavity filling, vital and non-vital dental pulp therapy, securing prosthetic and orthodontic devices, root-end filling, post or device cementation, dental ridge augmentation, pulp capping, root canal sealing, bone fixation, retention of separation of collapsed vertebrae, and replacement of missing bone.

4. The ceramic cement composition of claim 1 further characterized by formulations in which said tricalcium silicate is present in the range of 30% to 75% by weight for accelerated hydraulic setting into a hardened cement mass in teeth and bone within said initial maximum setting time of 5 minutes in teeth and bone for cavity filling, vital and non-vital dental pulp therapy, securing prosthetic and orthodontic devices, root-end filling, post or device cementation, dental ridge augmentation, pulp capping, root canal sealing, bone fixation, retention of separation of collapsed vertebrae, and replacement of missing bone.

5. The ceramic cement composition of claim 1 further characterized by formulations wherein said fine ceramic cement powder is present in the range of 40% to 85% by weight.

6. The ceramic cement composition of claim 1 further characterized said fine radiopaque powder present in the range of 15% to 60% by weight.

7. The ceramic cement composition of claim 1 further characterized by said blended powder mixed with a non-aqueous liquid to create a single, ready-to-use paste having said blended powder present in the range of 60% to 85% by weight that is fillable into and extrudable from a syringe.

8. The ceramic cement composition of claim 1 further characterized by single, ready-to-use paste further comprising nanoparticles of stabilizing silica and halloysite less than 100 nm (0.1 μm) in size, said nanoparticles providing a shelf-life of greater than one year without refrigeration for said single, ready-to-use paste, said nanoparticles also not causing dimensional change in said single, ready-to-use paste during setting, and said nanoparticles not causing dimensional change in said single, ready-to-use paste after setting.

9. The ceramic cement composition of claim 1 further characterized by a quantity of said fine ceramic cement powder stored as an unset cement paste after mixing with a non-aqueous liquid and a quantity of said fine radiopaque powder stored as an unset radiopaque paste after mixing with an aqueous liquid, in combination at an application site undergoing hydraulic setting to form a hardened cement mass.

10. The ceramic cement composition of claim 1 further characterized by said fine ceramic cement powder packaged in a first container and also further characterized by a second container with liquid to be mixed with said fine ceramic cement powder, whereinafter and according to need, said fine ceramic cement powder in said first container and said liquid in said second container may be combined into a custom formulation for use and applied in vivo for hydraulic setting.

11. The cement composition of claim 1 further characterized by said fine radiopaque powder selected from a group consisting of zinc oxide, zirconia, iodoform, calcium tungstate, cerium oxide, tantalum oxide, tungsten, barium sulfate, silver, gold, radiopaque silicate glasses containing a maximum amount of less than 60% by weight of baria or strontia, and radiopaque phosphate glasses containing a maximum amount of less than 60% by weight of baria or strontia.

12. The ceramic cement composition of claim 1 in a first container and an aqueous liquid in a second container, said aqueous liquid having at least one biocompatible, water-soluble polymer with a molecular weight less than 50,000, at least one water-miscible, biocompatible organic liquid, and at least one salt, such that when said powder in said first container and said liquid in said second container are mixed, the resulting unset paste has minimal bubbles to create a dense solid material after hydraulic setting occurs.

13. The ceramic cement composition of claim 1 further characterized by said blended powder in a first container and a second container holding an aqueous liquid with at least one biocompatible, water-soluble polymer having a molecular weight greater than 50,000, such that when said blended powder in said first container and said aqueous liquid with at least one biocompatible, water-soluble polymer in said second container are vigorously spatulated together into an unset paste, said unset paste is foamy and creates a porous solid after hydraulic setting occurs.

14. The ceramic cement composition of claim 1 further having characteristics selected from a group consisting of non-cytotoxic at least after setting, non-irritating, non-sensitizing, non-allergenic, non-mutagenic, elevated pH and calcium ion release for bioactivity, antibacterial, hydrophilicity to allow setting in the presence of moisture and blood, case of manipulation and placement, washout resistance, low heat of setting, low contact angle with tissues, sets under infected conditions that are acidic, will enter dentinal tubules and trabecular bone spaces for mechanical adhesion, promote cementogenesis and regeneration of bone and periodontal ligament, seal a site hermetically, conform to surrounding tissue, dimensional stability, non-discoloring, having bone-like coloring, having tooth-like coloring, having coloring that does not change over time, cost-effective, and acid-resistance greater than calcium silicate cement alone.

15. The ceramic cement composition of claim 1 further characterized by an initial setting time in the range of 2 to 5 minutes when said blended powder is placed in contact with at least one aqueous liquid in a powder-to-water ratio in the range of 4:1 to 2:1.

16. A method of using the composition of claim 1 in dental, medical, and veterinary application sites, said method comprising the steps of:
   a) providing a quantity of said fine blended powder, a dispensing container having a 30-gauge-sized orifice for dispensing, and a quantity of liquid which when mixed with said fine blended powder will create an unset paste;
   b) mixing said provided quantity of fine blended powder with said provided quantity of liquid until an unset paste is created;
   c) placing said created unset paste into said provided dispensing container; and
   d) releasing said unset paste from said dispensing container through said orifice into an application site selected from a group consisting of dental, medical, and veterinary application sites.

17. The method of claim 16 wherein said mixing of said quantity of said fine blended powder provided with said quantity of liquid provided to create an unset paste is further characterized by mechanical mixing with devices selected from a group consisting of mixing syringes, mixing tips for syringes, capsules, multicompartment foil pouches, and trituration capsules.

18. The method of using said blended powder of claim 1 in dental, medical, and veterinary application sites comprising the steps of:
   a) selecting an application site for use of said blended powder from a group consisting of dental, medical, and veterinary application sites;
   b) prior to delivery of said blended powder to said selected application site, providing a dispensing container having a 30-gauge-sized orifice for dispensing and a quantity of liquid which when mixed with said blended powder will create an unset paste;
   c) mixing said blended powder with said provided quantity of liquid until an unset paste is created;
   d) placing said created unset paste into said provided dispensing container;
   e) delivering said dispensing container with said unset paste therein to a clinician at said selected application site, and
   f) said clinician releasing said unset paste from said dispending container through said orifice into said selected application site for hydraulic setting into a hardened cement mass in vivo.

19. A method of using the composition of claim 1 in dental, medical, and veterinary application sites where biological fluids are present, said method comprising the steps of:
   a) providing a quantity of said blended powder from claim 1; and
   b) placing said blended powder into an application site with biological fluids present that is selected from a group consisting of dental, medical, and veterinary application sites wherein hydraulic setting of said provided quantity of said blended powder into a hardened cement mass occurs after contact of said blended powder with said biological fluids present at said selected application site.

20. A method of using said composition of claim 1, said method comprising the steps of:
   a) mechanical mixing of a first unset paste composed of said fine ceramic cement powder in claim 1 and non-aqueous liquid with a second unset paste composed of said fine radiopaque powder in claim 1 and aqueous liquid until a homogenous mixed paste is formed therefrom;
   b) selecting an application site for receiving said homogenous mixed paste from a group consisting of dental, medical, and veterinary application sites; and
   c) distributing said homogenous mixed paste at said selected application site for hydraulic setting thereof into a hardened cement mass.

* * * * *

UNITED STATES PATENT AND TRADEMARK OFFICE
CERTIFICATE OF CORRECTION

PATENT NO. : 12,171,898 B2  
APPLICATION NO. : 17/251192  
DATED : December 24, 2024  
INVENTOR(S) : Carolyn M Primus Page 1 of 1

It is certified that error appears in the above-identified patent and that said Letters Patent is hereby corrected as shown below:

In the Claims

Column 19, Line 24, that portion of Claim 1 reading "powder phase-having" should read --powder having--
Column 19, Lines 36-37, that portion of Claim 1 reading "where it applied" should read --where applied--
Column 20, Line 16, that portion of Claim 8 reading "claim 1 further" should read --claim 7 further--
Column 20, Line 17, that portion of Claim 8 reading "characterized by single" should read --characterized by said single--
Column 20, Line 59, that portion of Claim 12 reading "has minimal bubbles" should read --has sufficiently little bubbling--
Column 21, Line 10, that portion of Claim 14 reading "case of manipulation" should read --ease of manipulation--
Column 21, Line 49, that portion of Claim 18 reading "The method" should read --A method--
Column 22, Line 18, that portion of Claim 18 reading "dispending container" should read --dispensing container--
Column 22, Line 31, that portion of Claim 19 reading "sites wherein" should read --sites; wherein--
Column 22, Lines 39-40, that portion of Claim 20 reading "and non-aqueous liquid" should read --and a non-aqueous liquid--
Column 22, Lines 41-42, that portion of Claim 20 reading "and aqueous liquid" should read --and an aqueous liquid--

Signed and Sealed this  
Fifteenth Day of April, 2025

Coke Morgan Stewart  
*Acting Director of the United States Patent and Trademark Office*